United States Patent [19]
Muhler et al.

[11] 4,108,979
[45] Aug. 22, 1978

[54] DENTIFRICE PREPARATIONS COMPRISING ALUMINUM AND A COMPATIBLE ABRASIVE

[75] Inventors: Joseph C. Muhler, Howe; Mark S. Putt; Carl J. Kleber, both of Fort Wayne, all of Ind.

[73] Assignee: Indiana University Foundation, Bloomington, Ind.

[21] Appl. No.: 710,438

[22] Filed: Aug. 2, 1976

[51] Int. Cl.$^2$ ............................................. A61K 7/16
[52] U.S. Cl. ........................................ 424/49; 424/52
[58] Field of Search ................................ 424/49–58; 51/307–309

[56] References Cited

U.S. PATENT DOCUMENTS

| | | | |
|---|---|---|---|
| 906,339 | 12/1908 | Tone | 51/308 |
| 1,128,287 | 2/1915 | Carmichael | 51/307 |
| 1,444,479 | 2/1923 | Olson | 51/307 |
| 1,951,555 | 3/1934 | Masin | 51/308 |
| 2,256,528 | 9/1941 | Rowe et al. | 51/308 |
| 2,399,237 | 4/1946 | Maloney | 51/308 |
| 2,441,534 | 5/1948 | Norton | 51/308 |
| 2,541,658 | 2/1951 | Masin et al. | 51/307 |
| 3,095,356 | 6/1963 | Moss | 424/52 |
| 3,105,013 | 9/1963 | Saul et al. | 424/52 |
| 3,282,792 | 11/1966 | Fiscella | 424/52 |

FOREIGN PATENT DOCUMENTS

| | | |
|---|---|---|
| 829,272 | 12/1969 | Canada. |
| 3,610M | 11/1965 | France. |
| 1,273,859 | 2/1962 | France. |
| 176,091 | 4/1948 | Japan. |
| 74/24,224 | 6/1974 | Japan. |
| 1,287,758 | 9/1972 | United Kingdom. |

OTHER PUBLICATIONS

Gerhardt et al., J. Dent. Res. 51(3):870 May–Jun. 1972, "Fluoride Uptake in Natural Tooth Surfaces Pretreated with Aluminum Nitrate".

Ericsson et al., Chem. Abstr. 59 # 7315c (1963) "Aluminum Compounds in Fluorinated Toothpastes and Dental Prophylaxis Pastes".

Koren et al., Chem. Abstr. 69 # 99376m (1968) "Abrasive Properties of Some Domestic Toothpastes and Powders".

*Primary Examiner*—Shep K. Rose
*Attorney, Agent, or Firm*—Kirkland & Ellis

[57] ABSTRACT

Improved therapeutic dentifrice preparations comprise a nontoxic and anticariogenically effective amount of one or more water-soluble aluminum salts and a compatible dental abrasive selected from the group consisting of purified, calcined kaolin, calcined aluminum silicate, zirconium silicate, silica, alumina, calcined and uncalcined talcs, barium sulfate, resin abrasives, and mixtures thereof.

10 Claims, No Drawings

DENTIFRICE PREPARATIONS COMPRISING ALUMINUM AND A COMPATIBLE ABRASIVE

BACKGROUND OF THE INVENTION

1. Field of the Invention

This invention relates to therapeutic dentifrice formulations and in particular to dentifrice preparations comprising a soluble source of aluminum ions and a compatible dental abrasive material.

2. Description of the Prior Art

It is commonly recognized that the presence of small amounts of fluoride occurring naturally in drinking water (e.g., 1.0 microgram fluoride per milliliter) has a pronounced effect in reducing the incidence of dental caries in permanent teeth of children consuming such water from birth through eight years of age. Fluoride salts have been introduced into public water supplies in many communities with similar results. This method of dental caries prophylaxis is not available, however, to large numbers of people whose drinking water is obtained from small, private, fluoride-deficient sources such as individual wells and the like. Further, the addition of fluoride to common public water sources is not always accepted or permitted.

Topical application of aqueous fluoride solutions by dentists or dental hygienists likewise provide an excellent measure of protection against dental caries. Various fluoride compounds have been employed in this manner, including, stannous fluoride and sodium fluoride. Another method of employing the anticariogenic properties of fluoride salts comprises incorporating such materials with a compatible abrasive to form a prophylactic paste composition for use by dentists or dental hygienists on a professional basis.

Limitations on the availability of fluoride therapy by way of water supply or professional treatment has led to extensive efforts to incorporate fluoride salts in oral compositions for use in the home in the form of fluoride-containing dentifrices. Although effective dental caries protection has been obtained through the use of the aforementioned fluoride-containing compounds, occasional side effects have been experienced with certain of the known fluoride-containing anticariogenic agents, particularly certain tin-containing salts. For example, a brownish pigmentation of carious or precarious lesions has been experienced after anticariogenic agents containing the stannous ion have been applied to the teeth when the teeth are not properly cleaned with a toothbrush. Although the stain is not necessarily undesirable from a physiological standpoint, nevertheless, for esthetic reasons it would be desirable to provide an effective anticariogenic agent that does not pigment carious enamel.

The utility of certain of the prior art anticariogenic fluoride materials has also been limited by the extent of their solubility in aqueous media. For example, sodium fluoride is only soluble to the extent of about 4% in water.

Furthermore, because of the concern from a toxicity standpoint, current regulations imposed by the U.S. Food and Drug Administration limit the amount of fluoride that can be provided in products sold for over-the-counter use.

Finally, certain of the known prior art anticariogenic agents have been relatively unstable in aqueous solution. For example, stannous fluoride is subject to both oxidation and hydrolysis and for that reason must be used in freshly prepared form and must be used in conjunction with complexing anions in order to obtain its optimal anticariogenic effect.

As a result, dental researchers have continued the search for other anticariogenic agents to use in place of or in addition to fluoride-containing anticariogenic adjuvants. It has been suggested that aluminum salts may have a beneficial effect in reducing dental caries or in facilitating the uptake of fluoride by the dental enamel. See, e.g., Manly et al., "Substances Capable of Decreasing the Acid Solubility of Tooth Enamel", J. Dent. Res. 28; 160 (1948); Regolati, et al., "Effects of Aluminum and Fluoride on Caries, Fluorine Content and Dissolution of Rat Molars", Hev. Odont. Acta. 13: 59 (1969); and Kelada, "Electrochemical Characteristics of Free and Complexed Fluorides in Drinking Water and The Effects of Aluminum and Iron on Fluoride Incorporation Into Tooth Enamel," Univ. Michigan Thesis (1972).

In vitro studies have shown that pretreatment of enamel with aluminum solutions resulted in increased fluoride uptake when followed by treatment with a fluoride solution; however, treatment with combinations of aluminum and fluoride did not afford any added benefit over that of fluoride alone. McCann, "The Effect of Fluoride Complex Formation on Fluoride Uptake and Retention in Human Enamel", Archs. Oral Biol. 14:521 (1969); and Gerhardt, et al., "Fluoride Uptake in Natural Tooth Surfaces Pretreated with Aluminum Nitrate", J. Dent. Res. 51:870 (1972). Moreover, the foregoing techniques have dealt primarily wth the use of aluminum in combination with fluorides in acidic media and have not focussed on the effect of aluminum in the absence of fluoride and in alkaline media.

Thus, while some elements are known to inhibit dental caries (e.g., F, Mo, Sr, and V) and while others are known to promote dental caries (e.g., Se, Mg, and Cd), the preponderance of data on aluminum indicate that it is caries inert as classified by Navia, "Effect of Minerals on Dental Caries", in *Dietary Chemicals vs. Dental Caries*, A.C.S., Washington, D.C. (1970).

Nor has the use of aluminum salts in dentifrices demonstrated the desired result, primarily because it has not been recognized that conventional dentifrice constituents such as abrasives are incompatible with sources of biologically available aluminum. Thus, while French Pat. No. 3610M describes a specific combination of aluminum lactate, aluminum fluoride and calcium pyrophosphate, the abrasive interferes with the aluminum by reacting therewith to form insoluble aluminum phosphate. Similarly, U.S. Pat. No. 3,095,356 uses aluminum salts such as aluminum fluoride to coact with insoluble sodium metaphosphate abrasives to reduce the solubility of such abrasives and to increase fluoride uptake, but without independent therapeutic advantage being taken of the aluminum.

Canadian Pat. No. 829,272 describes acidic dentifrices comprising a combination of surface active substances and albumen coagulating substances such as certain carboxylic acid salts of aluminum and other metals. However, this patent likewise fails to teach that the satisfactory use of aluminum ions in dentifrices is dependent upon the use of aluminum-compatible constituents or that significant dental health benefits can be achieved with alkaline aluminum systems.

Thus, the prior art has not heretofore suggested a therapeutically effective aluminum system which provides biologically available aluminum as an anticariogenic oral composition.

Accordingly, it is a primary object of this invention to produce oral compositions incorporating a soluble source of aluminum ions and a compatible abrasive system which provides the aluminum ions to be presented in a therapeutically effective biologically available form in the oral cavity.

A related object of the present invention is to provide new and improved anticariogenic dentifrice preparations which need not contain fluoride ions.

A still further object of the present invention is to provide new and improved anticariogenic dentifrices.

SUMMARY OF THE INVENTION

The foregoing and other objects, advantages, and features of the subject invention may be achieved with dentifrice preparations comprising an anticariogenically effective and non-toxic amount of at least one water-soluble aluminum salt and a compatible dental abrasive selected from the group consisting of purified, calcined kaolin, calcined aluminum silicate, zirconium silicate, silica, alumina, resin abrasives, calcined and uncalcined talcs, barium sulfate and mixtures thereof.

Through the use of such dentifrice preparations, significant reductions of the incidence and severity of dental caries may be expected. In particular, the dentifrice preparations of this invention for the first time permit the benefits of oral aluminum therapy to be achieved.

DESCRIPTION OF THE PREFERRED EMBODIMENTS

In accordance with the subject invention, it has been found that new and improved therapeutic anticariogenic dentifrice preparations comprise an anticariogenically effective and non-toxic amount of at least one water-soluble aluminum salt and a compatible dental abrasive material selected from the group consisting of purified, calcined kaolin, calcined aluminum silicate, zirconium silicate, silica, alumina, resin abrasives, calcined and uncalcined talcs, barium sulfate, and mixtures thereof.

The particular water-soluble aluminum salt employed is not critical, and substantially any non-toxic, water-soluble aluminum ion containing salt may be used. Suitable aluminum salts include aluminum potassium sulfate, $AlK(SO_4)_2.12H_2O$; aluminum chloride, $AlCl_3.6H_2O$; aluminum sodium sulfate, $AlNa(SO_4)_2.12H_2O$; aluminum ammonium sulfate, $AlNH_4(SO_4)_2.12H_2O$; aluminum sodium phosphate $NaAl_3H_{14}(PO_4)_8.4H_2O$; aluminum sulfate, $Al_2(SO_4)_3.18H_2O$; aluminum nitrate, $Al(NO_3)_3.9H_2O$; and sodium aluminate, $NaAl(OH)_4$. Mixtures of such salts may be used. Aluminum potassium sulfate and aluminum chloride are preferred by reason of their wide availability and well established safety.

The anticariogenically effective and non-toxic amount of the soluble aluminum salt should lie in the range capable of supply about 10ppm up to about 50,000ppm aluminum ions (0.001 - 5.0 weight percent, calculated as aluminum ion). The preferred aluminum concentration range is from about 25ppm to about 10,000ppm Al most preferably, about 100-4000ppm Al. Thus, where aluminum potassium sulfate dodecahydrate and aluminum chloride hexahydrate are employed, the respective salts are present in the range of about 0.02% up to about 75% and about 0.01% up to about 45% by weight.

As mentioned, the dentifrice preparations of this invention are predicated on the discovery of a class of abrasive materials that are unusually compatible with aluminum ions sources. The preferred abrasive material for use in accordance with this invention comprises purified, calcined Kaolin abrasives as described and claimed in applicants' copending application entitled "DENTIFRICE PREPARATIONS COMPRISING PURIFIED, CALCINED KAOLIN ABRASIVES", Ser. No. 710,444 filed herewith. Other suitable abrasives that may be employed include calcined aluminum silicate abrasives of the type described in U.S. Pat. No. 3,105,013; zirconium silicate as described in U.S. Pat. No. 3,450,813; calcined and uncalcined talcs, $Mg_3Si_4O_{10}(OH)_2$; barium sulfate, $BaSO_4$; alumina, $Al_2O_3$; and resin abrasives as described in U.S. Pat. No. 3,070,510. Silicas such as silica gels or precipitated silicas and mixtures thereof with fumed silicas may also be employed. Mixtures of such abrasives may also be utilized.

The compatible dental abrasive material is provided in the dentifrice preparation at a level of about 0 - 95% by weight depending on the particular formulation desired. Toothpastes preferably contain a total of about 20 - 70% cleaning and polishing agent by weight, while tooth powders contain about 60 - 90% cleaning and polishing agent by weight. Gel-type dentifrices typically utilize about 20 - 40% abrasive by weight.

Dentifrice preparations utilizing the cleaning and polishing agents of the subject invention are prepared in a conventional manner and usually include additional ingredients which render the over-all composition commercially acceptable to consumers.

Thus, toothpastes required a binder substance to impart desired textural properties. Alkoxylated cellulose derivatives, nonionic agents resulting from the addition of ethylene oxide to a condensation product of propylene oxide and propylene glycol, natural gum binders such as gum tragancanth, gum karaya, gum arabic, etc., and seaweed derivatives such as Irish Moss and alginates, and water-soluble cellulose derivatives, such as sodium carboxymethyl cellulose can be used for this purpose. Synthetic colloidal magnesium silicate, such as "Laponite", also may be used and is preferred in gel-type formulations. Desirably, those materials are employed which are most compatible with aluminum ions, improvements in texture can also be attained by including an additional material such as colloidal magnesium aluminum silicate or colloidal silica. Binders in an amount of from 0.5% to 5.0%, by weight, can be used to form a satisfactory toothpaste.

Toothpastes conventionally contain sudsing agents. Suitable sudsing agents include, but are not limited to, water-soluble alkyl sulfates having from 8 to 18 carbon atoms in the alkyl radical, such as sodium lauryl sulfate, ethoxylated fatty ethers or ethoxylated fatty alcohol esters, water-soluble salts of sulfonated monoglycerides of fatty acids having from 10 to 18 carbon atoms in the alkyl radical such as sodium coconut monoglyceride sulfonate, salts of fatty acid amides of taurines such as sodium-N-methyl palmitoyl taurine, nonionic surfactants, and salts of fatty acids esters of isethionic acid. Sudsing agents can be used in the compositions of this invention in an amount of from about 0.5% to about 5.0%, by weight, of the total composition.

It is also desirable to include some humectant material in a toothpaste to prevent hardening. Materials commonly used for this purpose include glycerine, sorbitol, and other polyhydric alcohols. The humectants can comprise up to 35% of conventional toothpaste compositions. In the case of gel-type formulations, humectants may be used at levels as high as 80%, by weight.

Finally, flavoring materials may be included in a toothpaste formulation including small amounts of oils of wintergreen and peppermint and sweetening agents such as saccharin, dextrose, and levulose.

In all cases, the additional ingredients provided in such dentifrice preparations are selected so as to be compatible with the aluminum ions.

While dentifrices of this invention may be employed at their natural pH values which lie in the range of about 2.5 – 4.5, it is generally desirable that the pH be adjusted in the range of about 4.0 – 5.0 with acetic acid or other buffering agents. Because of the insolubility of aluminum hydroxide, an alkaline pH may be advantageously used with these aluminum agents only through the use of additional constituents that act to retain the aluminum in available form in a basic environment. One such approach is described in applicants' co-pending application entitled "ORAL COMPOSITIONS COMPRISING ALUMINUM AND CARBOXYLIC ACIDS", Ser. No. 710,439 filed herewith.

As previously indicated, the dentifrices of the present invention may also contain water-soluble fluoride-containing anticariogenic adjuvants. Preferably such an adjuvant is present in the form of water-soluble fluoride-containing compounds capable of supplying fluoride ions, the preferred adjuvant is sodium fluoride, NaF, although other materials such as stannous fluorozirconate ($SnZrF_6$), indium fluorozirconate ($InZrF_7$), stannous fluoride ($SnF_2$), and complex zirconium-germanium fluorides (e.g., $Zr(GeF_6)_2$, $ZrGeF_8$, $Ge(ZrF_6)_2$, and $ZrOGeF_6$) may be employed. Sodium fluoride is preferred by virtue of the absence of objectionable taste, lack of enamel pigmentation, and the freedom from damage to gingival tissue, and by reason of anticariogenic effectiveness obtainable therewith.

Other suitable adjuvants include water-soluble fluoride salts such as $NH_4F$, $SnF_4$, $KF$, $InF_3$, $PbF_2$, $FeF_2$, and $LiF$, as well as more complex water-soluble fluoride-containing adjuvants such as fluorosilicates, e.g., $Na_2SiF_6$, other fluorozirconates, e.g., $CaZrF_6$, $Na_2ZrF_6$, $K_2ZrF_6$, fluorostannites, e.g., $NaSnF_3$, fluoroborates, e.g., $NaBF_4$, fluorotitanates, e.g., $NaTiF_5$, other fluorogermanates, e.g., $K_2GeF_6$, and mixed halides, e.g., $SnClF$ and $Sn_2ClF_3$. Mixtures of $GeF_6$ suitable adjuvants may also be utilized. Aluminum fluoride, $AlF_3$, may be used to supply both aluminum and fluoride to the system.

In general, such fluoride adjuvants are present in anticariogenically effective and non-toxic amounts, typically at a level of about 0.05 up to 1.0%, by weight, of the dentifrice preparation so as to provide up to about 1000 ppm fluoride ion. Sodium fluoride is preferably provided at a level of 0.22%, by weight, and when $SnF_2$ is utilized, the desired amount is preferably about 0.4%.

Compositions of exemplary dentifrice preparations in accordance with the present invention are given in the following Examples.

EXAMPLE I

| Constituent | Parts by Weight |
| --- | --- |
| Purified, calcined kaolin | 37.00 |
| Aluminum chloride | 1.79 |
| Water | 24.71 |
| Glycerine | 14.00 |
| Sorbitol | 17.50 |
| Hydroxyethylated-carboxymethyl cellulose | 1.50 |
| Polysorbate 80, polyoxyethylene 20 sorbitanmonoaleate | 1.50 |
| Flavorings, sweetener, coloring, etc. | 2.00 |
| | 100.00 |

EXAMPLE II

| Constituent | Parts by Weight |
| --- | --- |
| Calcined aluminum silicate | 37.00 |
| Aluminum potassium sulfate | 1.02 |
| Sodium fluoride | 0.22 |
| Water | 25.26 |
| Sorbitol | 17.50 |
| Glycerine | 14.00 |
| Xanthan gum | 1.50 |
| Sodium lauryl sulfate | 1.50 |
| Flavoring, sweetener, preservatives, etc. | 2.00 |
| | 100.00 |

EXAMPLE III

| Constituent | Parts by Weight |
| --- | --- |
| Zirconium silicate | 37.00 |
| Aluminum nitrate | 0.81 |
| Sodium fluoride | 0.22 |
| Water | 25.47 |
| Sorbitol | 17.50 |
| Glycerine | 14.00 |
| Xanthan gum, Keltrol | 1.50 |
| Sodium lauryl sulfate | 1.50 |
| Flavoring, sweeteners, preservatives, coloring, etc. | 2.00 |
| | 100.00 |

EXAMPLE IV

| Constituent | Parts by Weight |
| --- | --- |
| Calcined talc | 40.00 |
| Aluminum chloride | 0.45 |
| Aluminum fluoride | 0.24 |
| Water | 22.81 |
| Glycerine | 14.00 |
| Sorbitol | 17.50 |
| Xanthan gum | 1.50 |
| Sodium lauryl sulfate | 1.50 |
| Sweeteners, flavorings, coloring, preservatives | 2.00 |
| | 100.00 |

EXAMPLE V

| Constituent | Parts by Weight |
| --- | --- |
| Uncalcined talc | 40.00 |
| Sodium aluminate | 0.44 |
| Water | 21.69 |
| Hydrochloric acid (37.5%) | 1.37 |
| Glycerine | 14.00 |
| Sorbitol | 17.50 |
| Hydroxyethylated carboxymethyl cellulose | 1.50 |
| Polysorbate 80 | 1.50 |
| Colorings, preservatives, flavorings, etc. | 2.00 |
| | 100.00 |

EXAMPLE VI

| Constituent | Parts by Weight |
| --- | --- |
| Alumina | 37.00 |
| Aluminum sodium sulfate | 1.70 |
| Water | 24.80 |
| Glycerine | 14.00 |
| Sorbitol | 17.50 |
| Hydroxyethylated carboxymethyl | 1.50 |

EXAMPLE VI-continued

| Constituent | Parts by Weight |
|---|---|
| cellulose | |
| Polysorbate 80 | 1.50 |
| Flavors, colors, etc. | 2.00 |
| | 100.00 |

Barium sulfate, resin abrasives, and abrasive mixtures may be substituted for the abrasive constituents given in the foregoing Examples.

Exemplary toothpowders and gel-type dentifrices are respectively given in the Examples VII and VIII.

EXAMPLE VII

| Constituent | Parts by Weight |
|---|---|
| Purified, calcined kaolin | 50.00 |
| Aluminum chloride | 1.79 |
| Fillers, flavors, etc. | 48.21 |
| | 100.00 |

EXAMPLE VIII

| Constituent | Parts by Weight |
|---|---|
| Precipitated silica or silica zerogel | 22.00 |
| Aluminum potassium sulfate | 1.02 |
| Sodium fluoride | 0.22 |
| Sorbitol | 64.16 |
| Glycerine | 4.50 |
| Water | 3.35 |
| Carboxymethyl cellulose | 0.20 |
| Laponite 2101 | 1.05 |
| Sodium lauryl sulfate | 1.50 |
| Flavoring, sweetener, etc. | 2.00 |
| | 100.00 |

EXPERIMENTAL EVALUATIONS

The effectiveness of the dentifrice preparations of this invention in providing aluminum in available form has been demonstrated by the following experimental evaluations. The study used 1000 ppm $Al^{+3}$ provided in the form of $AlCl_3.6H_2O$ in the presence of a number of abrasives.

In each case, 8 grams of abrasive were mixed with 20 milliliters of water containing 1000 ppm aluminum ion. The slurries were shaken for 20 minutes each and then centrifuged at 4,000 rpm until the supernatants were clear. The supernatants were then analyzed for aluminum ions using atomic absorption spectrophotometry. Three replicates were performed for each system. Aluminum availability data, expressed as a percentage of the amount initially provided, are given in the Table.

The aluminum availability data set forth in the Table demonstrate the surprising and unexpected levels of aluminum compatibility achieved with the abrasives of the present invention. In striking contrast, the data for other conventional dental abrasives such as calcium carbonate, calcium pyrophosphate, calcium dihydrogen phosphate and calcium dihydrogen phosphate dihydrate were uniformly unsatisfactory.

The ability of a system to reduce the decalcification of dental enamel is a phenomena measured by in vitro enamel solubility reduction "ESR" studies carried out in the following manner.

Sound central maxillary incisors were mounted in self-curing acrylic resin, with the labial surface exposed, and given a thorough prophylaxis with flour of pumice. A "window" was then formed on the labial surface by dripping wax over a 1.0 cm diameter aluminum foil circle. A sharp stylus was then used to circumscribe the foil window which was then removed exposing a round area of enamel of reproducible size.

The windowed teeth were decalcified 4 consecutive times over 20-minute intervals with 25 ml aliquots of a 0.2 N acetic acid solution (buffered to a pH of 4.0) at a stirring rate of 60 rpm using an ESR stirring apparatus. By the 4th decalcification, the amount of calcium and phosphorus being dimineralized from the teeth reach a constant level. The teeth were then treated with test materials obtained as follows.

Four grams of each abrasive to be tested were slurried with 10 ml of 1,000 ppm $Al^{+3}$ provided as $AlCl_3.6H_2O$. The slurry was diluted with 42 ml of distilled water, the pH was adjusted to 4.4 – 4.5 with HCl and NaOH, was mechanically shaken for 15 minutes, centrifuged for 20 minutes at 4,000 rpm and 25 ml of the supernatant liquid was used for the treatment.

After treatment the teeth were decalcified again with 25 ml portions of the acetic acid buffer for four additional 20-minute intervals. The 5th and 8th decalcification solutions are referred to as the first post-treatment decalcification (1st PTD) and 4th post-treatment decalcification (4th PTD), respectively.

The difference in the amount of calcium and phosphorus in the 4th decalcification solution before treatment and that present in the 5th and 8th decalcification solutions after treatment, divided by the amount of 4th decalcification, times 100 is used to determine the 1st PTD and 4th PTD ESR values. Calcium is determined using atomic absorption spectrophotometry, and phosphorus using the Fiske-Subbarow method.

ESR data were obtained for a number of dentifrice abrasives in accordance with this invention and these data are also reported in the Table. The ESR data of the Table are strongly supportive of the significant oral health advances that may be achieved by supplying a source of water-soluble aluminum ions in a dentifrice preparation employing abrasives in accordance with this invention. In particular, the difference in ESR data between the abrasives employed with this invention and such other well known and widely used abrasives as calcium pyrophosphate and calcium carbonate dramatically demonstrates the manner in which the systems of this invention permit the solubility of dental enamel to be reduced without using fluorides.

TABLE

| Abrasive Material | Percent Available $Al^{+3}$ Natural pH | Adjusted pH | | | | Natural pH | | | |
|---|---|---|---|---|---|---|---|---|---|
| | | Calcium ESR (%) | | Phosphorus ESR (%) | | Calcium ESR(%) | | Phosphorus ESR(%) | |
| | | 1st PTD | 4th PTD | 1st PTD | 4th PTD | 1st PTD | 4th PTD | 1st PTD | 4th PTD |
| Purified, Calcined Kaolin (Sample I) | 110 | 59 | 40 | 51 | 29 | 70 | 40 | 68 | 38 |
| Purified, Calcined Kaolin (Sample II) | 105 | 60 | 32 | 73 | 34 | 63 | 35 | 73 | 28 |
| Purified, Calcined Kaolin (Sample III) | 70 | 69 | 40 | 68 | 35 | 56 | 43 | 61 | 44 |
| Calcined Aluminum Silicate | 113 | 69 | 46 | 64 | 37 | 71 | 50 | 74 | 53 |
| Zirconium Silicate | 97 | 63 | 13 | 61 | 17 | 74 | 45 | 66 | 41 |

TABLE-continued

| Abrasive Material | Percent Available $Al^{+3}$ Natural pH | Adjusted pH | | | | Natural pH | | | |
|---|---|---|---|---|---|---|---|---|---|
| | | Calcium ESR (%) | | Phosphorus ESR (%) | | Calcium ESR(%) | | Phosphorus ESR(%) | |
| | | 1st PTD | 4th PTD | 1st PTD | 4th PTD | 1st PTD | 4th PTD | 1st PTD | 4th PTD |
| (Superpax A) Uncalcined Talc | 96 | 72 | 30 | 73 | 41 | 68 | 44 | 62 | 41 |
| Calcined Talc | 96 | 63 | 32 | 67 | 31 | 65 | 40 | 66 | 39 |
| Barium Sulfate | 100 | 72 | 29 | 76 | 35 | 85 | 70 | 80 | 65 |
| Calcium Carbonate | 0 | 21 | 1 | 20 | −16 | −17 | 0 | −20 | −3 |
| Insoluble Sodium Metaphosphate | 38 | 39 | −14 | 40 | −11 | 70 | 49 | 74 | 43 |
| Calcium Hydrogen Phosphate Dihydrate | 0 | 7 | −24 | 13 | −23 | 6 | −8 | −26 | −43 |
| Anhydrous Calcium Hydrogen Phosphate | 0 | −5 | −26 | −19 | −43 | −13 | −18 | −19 | −18 |
| Calcium Pyrophosphate | 31 | −13 | −78 | −22 | −80 | 53 | 13 | 54 | 22 |

We claim:

1. A method for reducing decalcification and solubility of dental enamel and the incidence and severity of dental caries comprising the application to the teeth of a fluoride-free dentifrice preparation comprising a nontoxic and anticariogenically effective amount of at least one water-soluble aluminum salt and a dental abrasive consisting essentially of a member selected from the group consisting of purified, calcined kaolin, calcined aluminum silicate, silica, alumina, and mixtures thereof.

2. A method, as claimed in claim 1, wherein the aluminum salt is provided at a level of about 0.001 - 5.0% by weight calculated as aluminum ions and the dental abrasive is present at a level of about 10–95% by weight of the preparation.

3. A method, as claimed in claim 1, wherein the aluminum salt is aluminum chloride hexahydrate.

4. A method, as claimed in claim 1, wherein the aluminum salt is aluminum potassium sulfate dodecahydrate.

5. A method, as claimed in claim 1, wherein the dental abrasive is purified, calcined kaolin.

6. A fluoride-free dentifrice preparation having a reduced potential for decalcifying dental enamel and that is effective to reduce the solubility thereof comprising a nontoxic and anticariogenically effective amount of at least one water-soluble aluminum salt and a dental abrasive consisting essentially of a member selected from the group consisting of purified, calcined kaolin, calcined aluminum silicate, silica, alumina, and mixtures thereof.

7. A dentifrice preparation, as claimed in claim 6, wherein the aluminum salt is provided at a level of about 0.001 - 5.0% by weight calculated as aluminum ions and the dental abrasive is present at a level of about 10–95% by weight of the preparation.

8. A dentifrice preparation, as claimed in claim 6, wherein the aluminum salt is aluminum chloride hexahydrate.

9. A dentifrice preparation, as claimed in claim 6, wherein the aluminum salt is aluminum potassium sulfate dodecahydrate.

10. A dentifrice preparation, as claimed in claim 6, wherein the dental abrasive is purified, calcined kaolin.

* * * * *